United States Patent

Creuzet et al.

[11] Patent Number: 4,721,715
[45] Date of Patent: Jan. 26, 1988

[54] DERIVATIVES OF 4-(ARYLPIPERAZINYL-ETHYLAMINOETHOXY) PHENOL USEFUL FOR EFFECTING HYPOLIPIDEMIC THERAPY OR CARDIOVASCULAR THERAPY

[75] Inventors: Marie-Hélène Creuzet, Bordeaux; Claude Feniou, Pessac; Francoise Guichard, Bordeaux; Henri Pontagnier, Pessac; Gisèle Prat, Talence, all of France

[73] Assignee: Societe Cortial, S.A., Paris, France

[21] Appl. No.: 763,257

[22] Filed: Aug. 7, 1985

[30] Foreign Application Priority Data

Aug. 7, 1984 [FR] France .................. 84 12580

[51] Int. Cl.$^4$ .................. A61K 31/495; C07D 241/04; C07D 401/04
[52] U.S. Cl. .................. 514/255; 544/360; 544/394
[58] Field of Search .................. 544/360, 394; 514/255

[56] References Cited

U.S. PATENT DOCUMENTS

| | | | |
|---|---|---|---|
| 3,701,777 | 10/1972 | Edenhofer et al. | 544/394 |
| 3,951,983 | 4/1976 | Danilewicz et al. | 544/394 |
| 4,252,804 | 2/1981 | Joullié et al. | 544/394 |

FOREIGN PATENT DOCUMENTS

| | | | |
|---|---|---|---|
| 2814168 | 5/1978 | Fed. Rep. of Germany | 544/394 |
| 1349636 | 2/1963 | France . | |
| 3734M | 1/1964 | France . | |
| 8024563 | 2/1983 | Japan | 544/360 |

OTHER PUBLICATIONS

J. Med. Chem., R. Ratouis et al (Mar. 1965), pp. 271–273, *Synthesis and Pharmacological Study of New Piperazine Derivatives*, III. Phenoxyalkylpiperazines.
Chimie Therapeutique, L. Cronenberger et al. (1966), pp. 289–291, *Synthese de Nouvelles N-(Aryloxyalkyl)-Piperazines*(').

Primary Examiner—Donald G. Daus
Assistant Examiner—Cecilia Shen
Attorney, Agent, or Firm—Oblon, Fisher, Spivak, McClelland & Maier

[57] ABSTRACT

Compounds of the formula (I):

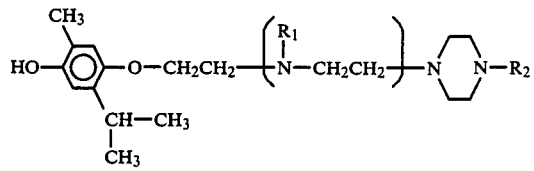

wherein n is 0 or 1, $R_1$ is H or a lower alkyl of 1 to 6 carbon atoms, $R_2$ is an unsubstituted phenyl group or a phenyl group substituted by one or more of the same or different substituents selected from the group consisting of hydroxy, lower alkyl of 1 to 6 carbon atoms, lower alkoxy of 1 to 6 carbon atoms, chloro, fluoro, trifluoromethyl or a 2-, 3- or 4- pyridyl ring, in the form of a free base or a pharmaceutically acceptable acid addition salt thereof.

The compounds of the present invention are useful in cardiovascular, antiallergy, psychotropic and hypolipidemic therapy.

8 Claims, No Drawings

DERIVATIVES OF 4-(ARYLPIPERAZINYL-ETHYLAMINOETHOXY) PHENOL USEFUL FOR EFFECTING HYPOLIPIDEMIC THERAPY OR CARDIOVASCULAR THERAPY

BACKGROUND OF THE INVENTION

1. Field of the Invention

The present invention relates to new phenoxypiperazinic derivatives, their method of preparation and therapeutic use.

2. Description of the Background

Compounds which can be classified as phenoxyalkylpiperazines are known. For example, R. Ratouis et al, *J. Med. Chem.*, describes some of these compounds having adrenolytic properties. Also, L. Cronenberger et al, *Chimie Therapeutique*, 5-6, 289-291 (1966) describe a synthesis of aryloxyalkylpiperazines, however no mention is made of any pharmacological activities.

Unfortunately, none of the known phenoxyalkylpiperazines possess sufficient adrenolytic properties to permit their use in therapy.

SUMMARY OF THE INVENTION

Accordingly, it is an object of the present invention to provide 4-(arylpiperazinylethylaminoethoxy)phenols which have a surprising array of therapeutic uses.

It is also an object of the present invention to provide a method for the preparation of these compounds.

Further, it is also an object of this invention to provide pharmaceutical compositions which contain the compounds of the present invention.

Moreover, it is also an object of this invention to provide methods of effecting cardiovascular therapy, anti-allergic therapy, psychotropic therapy and hypolipidemic therapy.

According to the present invention, the foregoing and other objects are attained by providing compounds having the formula (I)

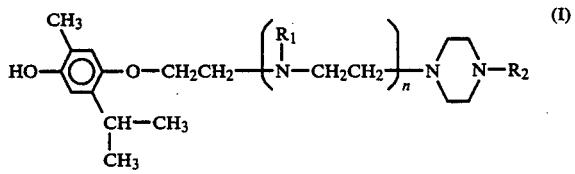

where n is 0 or 1, $R_1$ is a hydrogen atom or a lower alkyl group of 1 to 6 carbon atoms, $R_2$ is either an unsubstituted phenyl ring or a phenyl ring substituted by one or more substituents selected from the group consisting of hydroxy, lower alkyl of 1 to 6 carbon atoms, lower alkoxy having 1 to 6 carbon atoms, chlor, fluoro, trifluoromethyl or a 2-, 3- or 4-pyridyl ring; in the form or a free base of a pharmaceutically acceptable acid addition salt thereof.

DESCRIPTION OF THE PREFERRED EMBODIMENTS

According to the present invention, it has now been discovered that certain aryloxyalkylpiperazines are particularly useful in cardiovascular, psychotropic, hypolipidemic and anti-allergic therapy. In particular, it has been found that when such compounds are substituted in the phenoxy nucleus by a methyl at position 5, an isopropyl at position 2 and a hydroxy at position 4, the new products which are the subject of the present invention exhibit pharmacological properties which permit them to be used in human and veterinary therapy and particularly in cardiovascular, psychotropic, hypolipidemic and antiallergic therapy. With the term halo designating a bromine or chlorine atom in the following text, the products of formula I, where n=0, are generally prepared by a reaction involving a 4-(2-haloethoxy)-5-isopropyl-2-methyl phenol and an arylpiperazine having structural formula (II) in which $R_2$ represents either an unsubstituted phenyl ring or one substituted by one or more of the same or different substituents selected from the group of hydroxy, lower alkoxy of 1 to 6 carbon atoms, trifluoromethyl, chloro, fluoro or lower alkyl of 1 to 6 carbon atoms or a 2-, 3-, or 4-pyridyl ring.

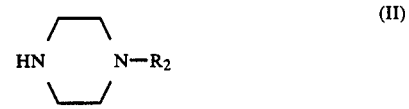

The products having structural formula (I), where n=1 are prepared by a reaction involving a 1-haloethyl-4-aryl piperazine having structural formula (III)

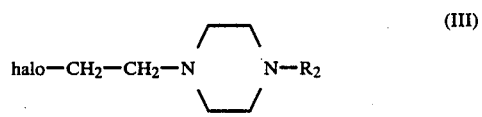

in which $R_2$ represents either an unsubstituted phenyl ring or one substituted by one or more of the same or different substituents selected from the hydroxy, lower alkoxy having 1 to 6 carbon atoms, trifluoromethyl, chloro, fluoro or lower alkyl having 1 to 6 carbon atoms, or a 2-, 3- or 4-pyridyl ring and a 5-isopropyl-2-methyl-4-aminoethoxy phenol having structural formula (IV):

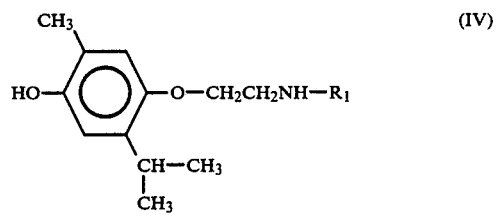

where $R_1$=H or a lower alkyl of 1 to 6 carbon atoms. The products of formula (I) such as where n=1 can also be prepared by a reaction involving a 1-aminoethyl-4-aryl piperazine with the formula (V)

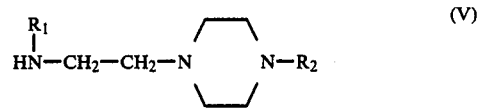

where $R_1$=H or a lower alkyl of 1 to 6 carbon atoms and $R_2$ represents either an unsubstituted phenyl ring or one substituted by one or more of the same or different substituents selected from the hydroxy, lower alkoxy of 1 to 6 carbons, trifluoromethyl, chloro, fluoro or lower alkyl of 1 to 6 carbons, or a 2-, 3- or 4-pyridyl ring and a 5-isopropyl-2-methyl-4-haloethoxy phenol having structural formula (VI)

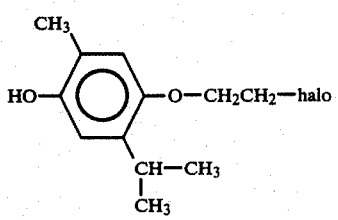

It should be noted that in all of the references to lower alkyl or lower alkoxy of 1 to 6 carbon atoms as described above, included, of course are methyl, ethyl, n-propyl, i-propyl, n-butyl, sec-butyl, t-butyl, n-pentyl and n-hexyl and the respective alkoxy moieties such as methoxy, ethoxy, n-propoxy, i-propoxy, n-butoxy, sec-butoxy, t-butoxy, n-pentoxy and n-hexoxy The present invention will now be further illustrated by certain examples which are provided for purposes of illustration only and are not intended to limit the present invention.

EXAMPLE 1

5-Isopropyl-2-methyl-4-(2-methoxyphenyl-piperazinyl)ethoxy)phenol hydrochloride or COR2831; hydrochloride of the product in formula (I) where n=0, $R_2$=2-methoxyphenyl.

Preparation

Quantities of 5.46 g 4-(2-bromoethoxy)-5-isopropyl-2-methyl phenol and 9.6 g (2-methoxyphenyl)piperazine are dissolved in 100 cc ethyl alcohol. This solution is heated in a reflux system for 12 hours without stirring. The solvent is evaporated. The residue is taken up in an aqueous hydrochloride solution. The brominated derivative which did not react is extracted with chloroform. The aqueous solution is neutralized with sodium hydroxide and extracted with chloroform. The chloroform solution is dried on sodium sulfate. The solvent is evaporated and the product obtained is purified by HPLC. Yield, 78%. The base is transformed into a hydrochloride by the action of the gaseous hydrochloric acid in solution in the chloroform.

Physiochemical Properties

Melting point of hydrochloride measured in the Mettler apparatus: 208° C.

NMR spectrum of hydrochloride in DMSOD$_6$: 1.2 ppm, 6 protons, duplet, $C(CH_3)_2$; 2.1 ppm, 3 protons, singlet, $CH_3$ at the phenyl ring; 2.9–4.0 ppm, 14 protons, complex mass, 5 $CH_2$—N+—CH—+$OCH_3$ at 3.8 ppm; 4.4 ppm, 2 protons, poorly formed triplet, $OCH_2$; 6.6–7.1 ppm, 6 protons, complex mass, aromatic protons; 5–10 ppm, 1 proton, very extended peak, OH, interchangeable with $D_2O$; 11.8 ppm, 1 proton, dome, NH+, interchangeable with $D_2O$.

EXAMPLE 2

5-Isopropyl-2-methyl-4-phenylpiperazinylethoxy-phenol hydrochloride or COR 2837; hydrochloride of the product in formula (I) where n=O, $R_2$=phenyl.

Preparation

A quantity of 2.5 equivalents of phenylpiperazine is added to a solution of 5.46 g 4-bromoethoxy-5-isopropyl-2-methylphenol in 100 ml ethyl alcohol. The reagent mixture is heated for six hours in a reflux system. The development of the reaction is followed by thin-layer silica chromatography with a mixture of chloroform 90/methanol 10 V/V as the elution solvent. After cooling, the phenylpiperazine hydrobromide is filtered. The filtrate is evaporated in a vacuum. The residue is taken up in a dilute ammonia solution and extracted with chloroform. The chloroform solution is evaporated. The residue obtained is taken up in a dilute hydrochloric acid solution. After extraction with chloroform, the precipitate formed is filtered and washed with a little ethyl ether; it is then purified by recrystallization. Yield, 56%.

Physiochemical Properties

Melting point of the hydrochloride measured on a Kofler apparatus: 190° C.

NMR spectrum of the hydrochloride in DMSOD$_6$: 1.1 ppm, 6 protons, duplet, $C(CH_3)_2$; 2.1 ppm, 3 protons, singlet, $CH_3$ at the phenyl ring; 3.0–3.9 ppm, 11 ppm, 11 protons, complex mass, 5 $CH_2$-N+—CH—; 4.4 ppm, 2 protons, poorly formed triplet, $OCH_2$: 6.6–7.5 ppm, 7 protons, complex mass, aromatic protons; 8.8 ppm, 1 proton, large peak, OH, interchangeable with $D_2O$; 11.7 ppm, 1 proton, dome, NH+, interchangeable with $D_2O$.

EXAMPLE 3

5-Isopropyl-2-methyl-4-(3-trifluoromethylphenyl) piperazinyl-ethoxy)phenol hydrochloride or COR 2839; hydrochloride of the product in formula (I) where n=0, $R_2$=3-trifluoromethylphenyl.

Preparation

A quantity of 2.5 equivalents of 3-trifluoromethyl phenyl-piperazine is added to a solution of 5.46 g 4-bromoethoxy-5-isopropyl-2-methylphenol in 100 ml ethyl alcohol. The reagent mixture is heated for 15 hours in a reflux system. The development of the reaction is followed by thin-layer silica chromatography using a mixture of chloroform 90/methanol 10 V/V as the elution solvent. After cooling, the 3-trifluoromethyl phenylpiperazine hydrobromide is filtered. The filtrate is evaporated in a vacuum. The residue is taken up in a dilute ammonia solution and extracted with chloroform. The chloroform is evaporated. The residue obtained is taken up in a dilute hydrochloric acid solution. After extraction with chloroform, the precipitate formed is filtered and washed with a little ethyl ether; it is subsequently purified by recyrstallization. Yield, 43%.

Physiochemical Properties

Melting point of the hydrochloride measured on a Kofler apparatus: 216° C.

NMR spectrum of hydrochloride in DMSOD$_6$: 1.2 ppm, 6 protons, duplet, $C(CH_3)_2$; 2.1 ppm, 3 protons, singlet, $CH_3$ at the phenyl ring; 3.0–4.6 ppm, 13 protons, complex mass, 6 $CH_2$+—CH—; 6.6–7.7 ppm, 6 protons, complex mass, aromatic protons; 8.8 ppm, 1 proton, dome, OH, interchangeable with $D_2O$; 11.8 ppm, 1 proton, dome, NH+, interchangeable with $D_2O$.

EXAMPLE 4

5-Isopropyl-2-methyl-4-(p-fluorophenylpiperazinylethoxy)phenol hydrochloride or COR 2841; hydrochloride of the product in formula (I) where n=0, $R_2$=4-fluorophenyl.

Preparation

A quantity of 2.5 equivalents of p-fluorophenylpiperazine is added to a solution of 5.46 g 4-bromoethoxy-5-isopropyl-2-methyl phenol in 100 ml ethyl alcohol. The reagent mixture is heated for 15 hours in a reflux system. The development of the reaction is followed by thin-layer silica chromatography with a mixture of chloroform 90/methanol 10 V/V as the elution solvent. After cooling, the p-fluorophenylpiperazine hydrobromide is filtered. The filtrate is evaporated in a vacuum. The residue is taken up in a dilute ammonia solution and extracted with chloroform. The chloroform solution is evaporated. The residue obtained is taken up in a dilute solution of hydrochloric acid. After extraction with chloroform, the precipitate formed is filtered and washed with a little ethyl ether; it is subsequently purified by recrystallization. Yield, 60%.

Physiochemical Properties

Melting point of the hydrochloride measured on a Kofler apparatus: 227° C.

NMR spectrum of hydrochloride in DMSOD$_6$: 1.2 ppm, 6 protons, duplet, C(CH$_3$)$_2$; 2.1 ppm, 3 protons, singlet, CH$_3$ at the phenyl ring; 2.9–4.7 ppm, 13 protons, complex mass, 6 CH$_2$+—CH—; 6.6–7.3 ppm, 6 protons, complex mass, aromatic protons; 8.8 ppm, 1 proton, extended peak, OH, interchangeable with D$_2$O; 11.9 ppm, 1 proton, dome, NH$^+$, interchangeable with D$_2$O.

EXAMPLE 5

5-Isopropyl-2-methyl-4-((3-chlorophenyl) piperazinylethoxy)phenol hydrochloride or COR 28 42; hydrochloride of product in formula (I) where n=0, R$_2$=3-chlorophenyl.

Preparation

A quantity of 2.5 equivalents of m-chlorophenylpiperazine is added to a solution of 5.46 g 4-bromoethoxy-5-isopropyl-2-methyl phenol in 100 ml ethyl alcohol. The reagent mixture is heated for 15 hours in a reflux system. The development of the reaction is followed by thin-layer silica chromatography with a mixture of chloroform 90/methanol 10 V/V as the elution solvent. After cooling, the m-chlorophenylpiperazine is filtered. The filtrate is evaporated in a vacuum. The residue is taken up in a dilute ammonia solution and extracted with chloroform. The chloroform solution is evaporated. The residue obtained is taken up in a dilute solution of hydrochloric acid. Following extraction with chloroform, the precipitate formed is filtered and washed with a little ethyl ether; it is subsequently purified by recrystallization. Yield, 47%.

Physiochemical Properties

Melting point of the hydrochloride measured on a Kofler apparatus: 224° C.

NMR spectrum of hydrochloride in DMSOD$_6$: 1.2 ppm, 6 protons, duplet, C(CH$_3$)$_2$; 2.1 ppm, 3 protons, singlet, CH$_3$ at the phenyl ring; 2.9–4.7 ppm, 13 protons, complex mass, 6 CH$_2$+—CH—; 6.6–7.4 ppm, 6 protons, complex mass, aromatic protons; 8.8 ppm, 1 proton, dome, OH, interchangeable with D$_2$O; 12.0 ppm, 1 proton, dome, NH$^+$, interchangeable with D$_2$O.

EXAMPLE 6

5-Isopropyl-2-methyl-4-(2-methylphenyl) piperazinylethoxy phenol hydrochloride or COR 2843; hydrochloride of the product in formula (I) in which n=0, R$_2$=2-methylphenyl.

Preparation

A quantity of 2.5 equivalents of (2-methylphenyl) piperazine is added to a solution of 5.46 g 4-bromoethoxy-5-isopropyl-2-methyl phenol in 100 ml ethyl alcohol. The reagent mixture is heated for 15 hours in a reflux system. The development of the reaction is followed by thin-layer silica chromatography with a mixture of chloroform 90/methanol 10 V/V as the elution solvent. After cooling, the (2-methylphenyl)piperazine hydrobromide is filtered. The filtrate is evaporated in a vacuum. The residue is taken up in a dilute ammonia solution and extracted with chloroform. The chloroform solution is evaporated. The residue obtained is taken up in a dilute solution of hydrochloric acid. The solution obtained is extracted with chloroform. The chloroform phase is washed with water, dried and then evaporated. The residue is washed with a little ethyl ether and then purified by recrystallization. Yield, 74%.

Physiochemical Properties

Melting point of the hydrochloride measured in a Kofler apparatus: 209° C.

NMR spectrum of hydrochloride in DMSOD$_6$: 1.2 ppm, 6 protons, duplet, C(CH$_3$)$_2$; 2.1 ppm, 3 protons, singlet, CH$_3$ at the phenyl ring; 2.3 ppm, 3 protons, singlet, CH$_3$ at the phenoxy ring; 2.3 ppm, 3 protons, singlet, CH$_3$ at the phenyl-piperazine ring; 2.9–4.6 ppm, 13 protons, complex mass, 6 CH$_2$+—CH—; 6.6–7.4 ppm, 6 protons, complex mass, aromatic protons; 8.8 ppm, 1 proton, dome, OH, interchangeable with D$_2$O; 11.9 ppm, 1 proton, dome, NH$^+$, interchangeable with D$_2$O.

EXAMPLE 7

5-Isopropyl-2-methyl-4-((N-methyl N-2-((2-methoxyphenyl)piperazinylethyl)amino)ethoxy phenol dihydrochloride or COR 2833; dihydrochloride of the product in formula (I) where n=1, R$_1$=CH$_3$, R$_2$=2-methoxyphenyl.

Preparation

A solution of 3.5 g 1-chloroethyl-4-(2-methoxyphenyl)piperazine and 3 g 5-isopropyl-2-methyl-4-methylaminoethoxy phenol in 100 ml ethyl alcohol is heated in a reflux system for six hours. The reaction is followed by thin-layer chromatography (chloroform/methanol 10%). The solvent is evaporated. The residue is taken up in an aqueous solution of hydrochloric acid. The solution obtained is extracted with chloroform. The aqueous phase is alkalized with ammonia and then extracted again with chloroform. The chloroform is dried and evaporated. The crude product is purified by silica chromatography, using chloroform as the eluent. The base is transformed into a hydrochloride with a saturated solution of ethyl ether in gaseous hydrochloric acid. The precipitate is filtered. Yield, 50%.

Physiochemical Properties

Melting point of the dihydrochloride measured in a Mettler apparatus: 90° C.

NMR spectrum of dihydrochloride in DMSOD$_6$: 1.1 ppm, 6 protons, duplet, C(CH$_3$)$_2$; 2.1 ppm, 3 protons, singlet, CH$_3$ at the phenyl ring; 2.8–4.1 ppm, 21 protons, complex mass, 7 CH$_2$—N+NCH$_3$ at 3.0 ppm +—CH—+OCH$_3$ at 3.8 ppm; 4.3 ppm, 2 protons, poorly formed triplet, OCH$_2$; 6.6–7.2 ppm, 6 protons, complex mass, aromatic protons; 6–8.5 ppm, 2 protons, very extended peak, unstable protons interchangeable with D$_2$O; 11.7 ppm, 1 proton, dome, NH+, interchangeable with D$_2$O.

EXAMPLE 8

5-Isopropyl-2-methyl-4-((N-methyl N-2-(phenyl-piperazinyl-ethyl)amino)ethoxy) phenol dihydrochloride or COR 2838; dihydrochloride of the product in formula (I) where n=1, R$_1$=CH$_3$, R$_2$=phenyl.

Preparation

A solution of 6 g 4-isopropyl-2-methyl-4-methylaminoethoxy phenol and 6 g 1-chloroethyl-4-phenylpiperazine in 10 ml triethylamine and 150 ml ethyl alcohol is heated for 20 hours in a reflux system. The excess ethyl alcohol and triethylamine are evaporated. The residue is taken up in an aqueous solution of hydrochloric acid. The solution obtained is extracted with chloroform. The aqueous phase is alkalized with ammonia and then extracted again with chloroform. After drying and evaporation of the chloroform, 9.3 g of crude product is obtained. This is purified by silica chromatography using as the eluent pure chloroform followed by a mixture of 98% chloroform and 2% methanol. This procedure yield 4.6 g of free base; yield, 42%. The latter is transformed into a hydrochloride by a saturated ethyl ether solution in gaseous hydrochloric acid. This produces a white solid which is filtered and washed with a little ethyl ether. The product is hygroscopic and soluble in water.

Physiochemical Properties

Melting point of the dihydrochloride measured in a Mettler apparatus: 152° C.

NMR spectrum of dihydrochloride in DMSOD$_6$: 1.1 ppm, 6 protons, duplet, C(CH$_3$)$_2$; 2.1 ppm, 3 protons, singlet, CH$_3$ at the phenyl ring; 2.8–4.6 ppm, 20 protons, complex mass, 8 CH$_2$—N+NCH$_3$ at 3.0 ppm +—CH—; 6.6–7.6 ppm, 7 protons, complex mass, aromatic protons; 8.8 ppm, 1 proton, very extended peak, OH, interchangeable with D$_2$O; 11.7 ppm, 2 protons, dome, NH+, interchangeable with D$_2$O.

EXAMPLE 9

5-Isopropyl-2-methyl-4-((4-methoxy phenyl-piperazinyl)ethoxy)phenol dihydrochloride or COR 2860; dihydrochloride of the product in formula (I) where n=0, R$_2$=4-methoxyphenyl.

Preparation

Quantities of 5.5 g 4-(2-bromoethoxy)-5-isopropyl-2-methyl phenol and 9.6 g (4-methoxyphenyl)piperazine are dissolved in 100 cc ethyl alcohol. This solution is stirred while heating for 12 hours in a reflux system. The solvent is evaporated in a vacuum. The residue is alkalized with a dilute ammonia solution and then extracted with chloroform. The chloroform solution is dried, the solvent is evaporated and the residue is taken up in a dilute solution of hydrochloric acid and then extracted with chloroform. The chloroform phase is washed, using a dilute solution of hydrochloric acid; it is then dried and evaporated. The crude product obtained in this manner is purified by recrystallization in a mixture of 40 ml methanol and 120 ml ethyl ether. Yield, 42%.

Physiochemical Properties

Melting point of the dihydrochloride measured in a Mettler apparatus: 181.9°–182.8° C.

NMR spectrum of dihydrochloride in DMSOD$_6$: 1.1 ppm, 6 protons, duplet, C(CH$_3$)$_2$; 2.1 ppm, 3 protons, singlet, CH$_3$ at the phenol ring; 2.9–4.9 ppm, 14 protons, complex mass, 5 CH$_2$—N+—CH—+OCH$_3$ at 3.7 ppm; 4.4 ppm, 2 protons, poorly formed triplet, OCH$_2$; 6.7 and 6.8 ppm, 2 protons, singlets, aromatic protons of phenol ring; 7.1 ppm, 4 protons, septanose AA"BB', aromatic protons of phenylpiperazine ring; 9.5–12.7 ppm, 3 protons, very extended peaks, unstable protons, interchangeable with D$_2$O.

EXAMPLE 10

5-Isopropyl-2-methyl-4-((2,3-dimethylphenyl-piperazinyl)ethoxy phenol hydrochloride or COR 2861; hydrochloride of the product in formula (I) where n=0, R$_2$=2,3-dimethylphenyl.

Preparation

A mixture consisting of 8.19 g 4-bromoethoxy-5-isopropyl-2-methyl phenol, 3.8 g (2,3-dimethylphenyl) piperazine, 100 ml ethyl alcohol and 40 ml triethylamine is heated for 12 hours in a reflux system. The reagent mixture is then evaporated in a vacuum and the residue taken up in a dilute ammonia solution and then extracted with chloroform. The chloroform solution is dried and evaporated. The residue obtained is taken up in a dilute solution of hydrochloric acid and then extracted with chloroform. The chloroform phase is washed with a dilute solution of hydrochloric acid and dried; the chloroform is evaporated. The liquid residue obtained is pulverized in ethyl ether. The raw solid is purified by recrystallization in 35 ml methanol. Yield, 49%.

Physiochemical Properties

Melting point of the hydrochloride measured in the Mettler apparatus: 234° C.

NMR spectrum of hydrochloride in DMSOD$_6$: 1.1 ppm, 6 protons, duplet, C(CH$_3$)$_2$; 2.1–2.2–2.23 ppm, 9 protons, singlets, 3 CH$_3$ at the phenyl rings; 2.9–4.0 ppm, 11 protons, complex mass, 5 CH$_2$—N+—CH—; 4.4 ppm, 2 protons, poorly formed triplet, OCH$_2$; 6.7 and 6.8 ppm, 2 protons, singlets, aromatic protons of phenol ring; 6.8–7.2 ppm, 3 protons, complex mass, aromatic protons of phenylpiperazine ring; 8.9 ppm, 1 proton, dome, OH, interchangeable with D$_2$O; 11.9 ppm, 1 proton, dome, NH+, interchangeable with D$_2$O.

EXAMPLE 11

5-Isopropyl-2-methyl-4-((2-chlorophenyl) piperazinylethoxy)phenol hydrochloride or COR 28 64; hydrochloride of the product in formula (I) in which n=0, R$_2$=2-chlorophenyl.

Preparation

The mixture consisting of 8.19 g 4-bromoethoxy-5-isopropyl-2-methyl phenol, 3.93 g (2-chlorophenyl) piperazine, 100 ml ethyl alcohol and 40 ml triethylamine is heated for 12 hours in a reflux system. The reagent mixture is then evaporated in a vacuum and the residue is taken up in a dilute ammonia solution and subsequently extracted with chloroform. The chloroform solution is dried and evaporated. The residue obtained is taken up in a dilute solution of hydrochloric acid and then extracted with chloroform; the chloroform phase is washed with water and dried on anhydrous sodium sulfate; the chloroform is evaporated. The solid obtained is crushed in ethyl ether to eliminate the excess brominated derivative and then purified by recrystallization in a mixture of methanol and ethyl ether. Yield, 26%.

Physiochemical Properties

Melting point of the hydrochloride measured in the Mettler apparatus: 205.2° C.

NMR spectrum of hydrochloride in DMSOD$_6$: 1.1 ppm, 6 protons, duplet, $C(CH_3)_2$; 2.1 ppm, 3 protons, singlet, $CH_3$ at the phenol ring; 2.9-4.0 ppm, 11 protons, complex mass, 5 $CH_2$ N+—CH—; 4.4 ppm, 2 protons, poorly formed triplet, $OCH_2$; 6.7 and 6.8 ppm, 2 protons, singlets, aromatic protons of the phenol ring; 6.9-7.7 ppm, 4 protons, complex mass, aromatic phenylpiperazine protons; 8.8 ppm, 1 proton, dome, OH, interchangeable with $D_2O$; 11.5 ppm, 1 proton, dome, NH+, interchangeable with $D_2O$.

EXAMPLE 12

5-Isopropyl-2-methyl-4-((2-ethoxyphenyl) piperazinylethoxy) phenol hydrochloride or COR 2865; hydrochloride of the product of formula (I) in which n=0, $R_2$=2-ethoxyphenyl.

Preparation

The mixture consisting of 8 g 4-(2-bromoethoxy)-5-isopropyl-2-methyl phenol, 6 g 4-(2-ethoxyphenyl) piperazine, 100 ml ethyl alcohol and 5 ml triethylamine is heated in an ethyl alcohol reflux system for six hours while stirring. The reaction is monitored by thin-layer chromatography using a 10/90 V/V mixture of methanol/chloroform as the eluent. The solvents are evaporated. 150 ml 1N hydrochloric acid is added to the evaporation residue; the mixture is stirred vigorously. The aqueous phase containing 4-(2-ethoxyphenyl) piperazine is eliminated. The viscous product is dissolved in methanol. A few drops of concentrated hydrochloric acid are added to the methanol solution which is concentrated in the Rotavapor. Ethyl ether is added in order to bring about precipitation of the product which is filtered and redissolved in methanol. Neutralization is effected with ammonia and the solvent is eliminated by evaporation. The evaporation residue is dissolved in chloroform; the solution is washed with water twice and dried on sodium sulfate. The chloroform is eliminated by evaporation. The product obtained is purified on a silica column, using chloroform as the initial eluent, followed by a 3% and then a 5% mixture of methanol/-chloroform. The product obtained is dissolved in ethyl ether. It is transformed into a hydrochloride by the addition of saturated ethyl ether in gaseous hydrochloric acid. The precipitate is filtered and then dried. Yield, 52%.

Physiochemical Properties

Melting point measured in the Mettler apparatus: 233.1°-233.6° C.

NMR spectrum of hydrochloride in DMSOD$_6$: 1.1 ppm, 6 protons, duplet, $C(CH_3)_2$; 1.4 ppm, 3 protons, triplet, $CH_3$ of the ethoxy group; 2.1 ppm, 3 protons, singlet, $CH_3$ at phenol ring; 2.9-4.7 ppm, 15 protons, complex mass, 7 $CH_2$+—CH—; 6.6-7.1 ppm, 6 protons, complex mass, aromatic protons; 8.8 ppm, 1 proton, dome, OH, interchangeable with $D_2O$; 11.7 ppm, 1 proton, dome, NH+, interchangeable with $D_2O$.

EXAMPLE 13

5-Isopropyl-2-methyl-4-((2-pyridyl)piperazinylethoxy) phenol dihydrochloride or COR 2873; dihydrochloride of the product in formula (I) in which n=0, $R_2$=2-pyridyl.

Preparation

The mixture consisting of 8.1 g 4-bromoethoxy-5-isopropyl-2-methyl phenol, 15 g 2-pyridyl piperazine and 100 ml ethyl alcohol is heated for eight hours in a reflux system while stirring. The precipitate is eliminated by filtration. The filtrate is evaporated in a vacuum. The evaporation residue is taken up in ethyl ether and extracted with a hydrochloric solution. The aqueous acid phase is alkalized, then extracted with chloroform. The chloroform phase is washed with water, dried on sodium sulfate and evaporated. The evaporation residue is dissolved in the smallest possible quantity of methanol. Ethyl ether is added again and the solution is saturated in gaseous hydrochloric acid. The precipitate formed is filtered and washed with ethyl ether. Yield, 38%.

Physiochemical Properties

Melting point of the dihydrochloride measured in the Mettler apparatus: 213.7°-215.2° C.

NMR spectrum of dihydrochloride in DMSOD$_6$: 1.1 ppm, 6 protons, duplet, $C(CH_3)_2$; 2.1 ppm, 3 protons, singlet, $CH_3$ at the phenyl ring; 2.9-5.2 ppm, 13 protons, complex mass, 6 $CH_2$+—CH—; 6.6-8.3 ppm, 6 protons, complex mass, aromatic protons, 10.1-13.2 ppm, 3 protons, extended peaks, OH+2 NH+, interchangeable with $D_2O$.

EXAMPLE 14

5-Isopropyl-2-methyl-4-(2-propoxyphenyl) piperazinylethoxy phenol hydrochloride or COR 2876; hydrochloride of the product in formula (I) in which n=0, $R_2$=2-propoxyphenyl.

Preparation

The mixture consisting of 15 g 4-bromoethoxy-5-isopropyl-2-methyl phenol, 200 ml ethyl alcohol, 8 g (2-propoxyphenyl) piperazine ans 20 ml triethylamine is heated for one night in a reflux system. The solvent is eliminated by evaporation. The residue is dissolved in chloroform. The solution is extracted twice with 1N hydrochloric acid to eliminate the (2-propoxyphenyl) piperazine which did not react. The chloroform solution is dried, and then evaporated. The residue obtained is taken up with ether and filtered. The solid phase is dissolved in methanol. The solution is neutralized with ammonia to a basic pH and then acidified with concentrated hydrochloric acid. The solvent is eliminated by evaporation. The residue is dissolved in chloroform. The chloroform phase is washed with water, dried, and subsequently evaporated. The residue is washed with a little ethyl ether and filtered. Yield, 73%.

Physiochemical Properties

Melting point of the hydrochloride measured in the Mettler apparatus: 223.2°-223.6° C.

NMR spectrum of the hydrochloride in DMSOD$_6$: 0.8–1.4 ppm, 9 protons, complex mass, C(CH$_3$)$_2$+CH$_3$ of the propoxy group; 1.8 ppm, 2 protons, multiplet, CCH$_2$C of the propoxy group; 2.1 ppm, 3 protons, singlet, CH$_3$ at the phenol ring; 2.9–4.7 ppm, 15 protons, complex mass, 7 CH$_2$ (piperazine +2 OCH$_2$C+NCH$_2$C)+—CH—; 6.6–7.2 ppm, 6 protons, complex mass, aromatic protons; 6–9 ppm, 1 proton, very extended peak, OH, interchangeable with D$_2$O; 12 ppm, 1 proton, dome, NH+, interchangeable with D$_2$O.

EXAMPLE 15

5-Isopropyl-2-methyl-4-(2-hydroxyphenyl) piperazinylethoxy phenol hydrochloride or COR 2877; hydrochloride of the product in formula (I) in which n=0, R$_2$=2-hydroxyphenyl.

Preparation

The mixture consisting of 20 g 4-bromoethoxy-5-isopropyl-2-methyl phenol, 150 ml ethyl alcohol, 10 g (2-hydroxyphenyl) piperazine and 20 ml triethylamine is heated for 12 hours in a reflux system. The solvent is removed by evaporation. Water is added to the residue followed by concentrated ammonia; two chloroform extractions are then performed. The chloroform solution is dried and evaporated. The residue obtained is taken up in 50 ml methanol. A stream of gaseous hydrochloric acid is passed into the solution so as to synthesize the hydrochloride. After cooling, the precipitate is filtered, and washed with methanol and then with ethyl ether. Yield, 68%.

Physiochemical Properties

Melting point of the hydrochloride measured in the Mettler apparatus: 279.1°–279.3° C.

NMR spectrum of hydrochloride in DMSOD$_6$: 1.1 ppm, 6 protons, duplet, C(CH$_3$)$_2$; 2.1 ppm, 3 protons, singlet, CH$_3$ at the phenoxy ring; 2.8–4.0 ppm, 11 protons, complex mass, 5 CH$_2$+—CH—; 4.4 ppm, 2 protons, poorly formed triplet, OCH$_2$; 6.6–7.1 ppm, 6 protons, complex mass, aromatic protons; 8.9 and 9.4 ppm, 2 protons, large peaks, 2 OH, interchangeable with D$_2$O; 11.5 ppm, 1 proton, very extended peak, NH+, interchangeable with D$_2$O.

The toxicological and pharmacological properties of the products according to the present invention will now be described.

Pharmacology and Toxicity

Toxicity: COR 2831, COR 2837, COR 2841, COR 2842, COR 2843, COR 2860, COR 2861 and COR 2864 caused no deaths when administered to mice in an oral dose of 300 mg/kg. When given to mice by the oral route, the LD$_{50}$ of COR 2831 is 1130 (1026–1246) mg/kg and that of COR 2865 is 1444 (1212–1719) mg/kg.

There were no deaths when COR 2831, COR 2837, COR 2839, COR 2831, COR 2842, COR 2843, COR 2860, COR 2861, COR 2864 and COR 2865 were given to mice in an intraperitoneal dose of 200 mg per kg and when COR 2838 was given in an IP dose of 50 mg/kg.

When administered to mice by the intravenous route, COR 2831 exhibited an LD$_{50}$ of 86 (76.6–98) mg/kg; COR 2865 caused no deaths at 6.2 mg/kg; it was responsible for a mortality rate of 10% at 12.5 mg/kg, 20% at 25 mg/kg, 5% at 50 mg/kg and 90% at 100 mg/kg.

Alpha-1 Blocking Activity: Alpha-1 blocking activity is evaluated in vitro by determination of the antagonism of contractions induced in isolated rabbit aorta strips by norepinephrine used in a concentration of $2.10^{-6}$ mol/l according to a technique derived from that described by Furchgott and Bhadrakom (J. Pharmacol. 108:129-43, 1953). The IC$_{50}$ (concentration inhibiting 50% of the contractions) as well as the interval between introduction of the test product and of the antagonist into the bath, which corresponds to the maximum activity, are presented below for the derivatives according to the present invention: COR 2831, 90 min, $1.10 \cdot 10^{-7}$ ($9.26 \cdot 10^{-8} - 1.31 \cdot 10^{-7}$) mol/l; COR 2837, 30 min, $1.64 \cdot 10^{-6}$ ($1.44 \cdot 10^{-6} - 1.85 \cdot 10^{-6}$) mol/l; COR 2841, 60 min, $1.16 \cdot 10^{-6}$ ($9.24 \cdot 10^{-7} - 1.46 \cdot 10^{-6}$) mol/l; COR 2843, 60 min, $9.82 \cdot 10^{-7}$ ($7.67 \cdot 10^{-7} - 1.26 \cdot 10^{-6}$) mol/l; COR 2838, 60 min, $2.53 \cdot 10^{-6}$ ($2.15 \cdot 10^{-6} - 2.98 \cdot 10^{-6}$) mol/l. The type of antagonism that COR 2831 exerts vis-a-vis norepinephrine was determined on the same type of preparation for an interval of 30 minutes, using the cumulative curve method according to Van Rossum in the presence of cocaine. The activity is of a competitive nature; the pA$_2$ calculated according to the method by Arunlakshama and Schild was 8.59±0.08.

Alpha-blocking activity was determined in vivo in mice with the test involving inhibition of mydriasis induced by norepinephrine. The animals were given the test product by the intraperitoneal route. Thirty minutes later, 0.75 mg/kg norepinephrine was administered intravenously. Under these conditions, when given in doses of 2.5 and 1 mg/kg, COR 2865, a noncholinergic product, produced 80% and 54% inhibition of mydriasis, respectively, while labetalol brings about 58% inhibition at 25 mg/kg. In vivo alpha-blocking activity was also evaluated by determination of antagonism of phenylephrine-induced hypertension. The test products were administered by the intravenous route to rats that had undergone spinal cord removal and bivagotomy according to the technique by J. S. Gillespie and T. S. Muir (Br. J. Pharmac. Chemother. 30:78-87, 1967). The dosage, maximum activity, and the interval after which residual activity was equal to 50% of the maximum activity are presented below:

COR 2831 ($3.10^{-6}$ M/kg — 129.2% — >2 hrs)
COR 2837 ($3.10^{-6}$ M/kg — 91.1% — 15 min)
COR 2841 ($3.10^{-6}$ M/kg — 39.8% — 15 min)
COR 2842 ($3.10^{-6}$ M/kg — 35.1% — 15 min)
COR 2843 ($3.10^{-6}$ M/kg — 112.3% — 25 min)
COR 2838 ($3.10^{-6}$ M/kg — 60% — 5 min)
COR 2860 ($3.10^{-6}$ M/kg — 39.7% — 4 min)
COR 2861 ($3.10^{-6}$ M/kg — 66.4% — 9 min)
COR 2864 ($3.10^{-6}$ M/kg — 98.6% — 37 min)
COR 2865 ($10^{-6}$ M/kg — 121.8% — 109 min) ($3.10^{-7}$ M/kg — 116.1% — 32 min)

The ED$_{50}$ determined under these conditions for COR 2831 was $1.95 \cdot 10^{-8}$ mol/kg after 2 min, $3.04 \cdot 10^{-7}$ mol/kg after 30 min and $8.4 \cdot 10^{-7}$ mol/kg after 60 min; for COR 2865, this parameter was $1.17 \cdot 10^{-8}$ mol/kg after 2 min, $3.18 \cdot 10^{-7}$ mol/kg after 30 min and $5.0 \cdot 10^{-7}$ mol/kg after 60 min.

Antihypertensive Activity: The test products were administered orally to spontaneously hypertensive rats. Arterial pressure was measured indirectly with a sphygmomanometer. For COR 2831 administered in a dose of 100 mg/kg/day for two days, the maximum pressure reductions were 26% and 21%, respectively, on the first and second days of therapy, one hour after gavage.

In another experiment that was also performed with oral administration in spontaneously hypertensive rats, arterial pressure was measured indirectly at the tail two, four and six hours after administration. For COR 2865 administered in a dose of 100 mg/kg, pressure reductions at these intervals were 19, 21 and 23%, respectively.

Hypoglycemic Activity: One hour after oral administration of a dose of 100 mg/kg, COR 2839 produced a 21% reduction in the glucose tolerance curve after an excess of starch (2.5 g per kg). One hour after oral administration of a dose of 100 mg per kg, COR 2839 brought about a decrease of 24% in the blook sugar of fasting mice subjected to an excess of glucose (1 g per kg) at the time that the test product was tiven.

Anticalcium Activity: On a left guinea pig auricle electrically stimulated to 150 beats/min in a Tyrode's solution with a low calcium content (0.6 mM), a does of $25.10^{-6}$ g/ml COR 2838 produced at 50% inhibition of the increment in the contraction force induced by addition of 0.6 mM calcium.

At $5.10^{-6}$ g/ml, COR 2838 inhibited the calcium-induced increment of spontaneous contractions in strips of mesenteric veins from rats with normal blood pressure.

COR 2838 brought about a 50% inhibition of contractions induced in isolated rabbit aorta by $60.10^{-6}$ M potassium chloride at a concentration of $9.44 \cdot 10^{-7}$ M/1 according to the technique by Karaki (Br. J. Pharmac. 77:661-666, 1982).

Antiallergy-Antihistamine Activity: In the passive cutaneous anaphylaxis test, COR 2833 and COR 2838 given to rats in an intravenous dose of 10 mg/kg produced 53 and 60% activity, respectively. Under the same conditions, COR 2831 produced 67% activity in an oral dose of 5 mg/kg.

COR 2831 and COR 2838 used in vitro in a concentration of $10^{-5}$ g/ml and COR 2833 in a concentration of $2.10^{-6}$ produced an 80% inhibition of the contractions induced in isolated guinea pig ileum by $5.10^{-7}$ g/ml histamine. When the ileum contractions were induced by $10^{-8}$ g/ml histamine and the test product was introduced in the bath ten minutes before the histamine, COR 2831 exhibited an $IC_{50}$ of $3.26 \cdot 10^{-6}$ $(2.68 \cdot 10^{-6} - 4.03 \cdot 10^{-6})$ M/1.

Antihistamine-antiallergy activity was also determined by combining an anaphylactic reaction (IgE) and a cutaneous histamine reaction in the same animal (Sprague-Dawley rat). Activity was evaluated by the quantity of Evans blue liberated at each reaction site as compared with control animals receiving the administration vehicle. COR 2831 produced the following $ED_{50}$ values in this test:

| Oral route | IgE | 14.4 | (7.7-27) | mg/kg |
|---|---|---|---|---|
|  | Histamine | 8.0 | (4.3-15) | mg/kg |
| IV route | IgE | 0.27 | (0.18-0.40) | mg/kg |
|  | Histamine | 0.37 | (0.21-0.62) | mg/kg |

Antiserotonin Activity: In vitro, contractions induced in isolated guinea pig ileum by $10^{-6}$ g/ml serotonin were inhibited by COR 2838 in a concentration of $4.10^{-7}$ g/ml and COR 2831 and COR 2833 in a concentration of $2.10^{-6}$ g/ml. When the ileum contractions were induced by $5.10^{-7}$ g/ml serotonin and the test product was introduced in the bath 15 minutes before the agonist, COR 2831 exhibited an $IC_{50}$ of $2.74$ $(1.89-3.99) \cdot 10^{-6}$ M/1.

The neuroleptic activity of COR 2865 was determined in the climbing test. Preselected mice placed in cages specially prepared for the test were given the test product by the intraperitoneal route; their climbing behavior was rated 0 to 2 during the 30 minutes following the injection. The animals did not exhibit any significant agonistic effect. They were given 1.5 mg/kg apomorphine in order to induce a maximum climbing level. Under these conditions, 25 mg/kg and 10 mg per kg COR 2865 produced, respectively, 100% and 83% inhibition of the climbing induced by apomorphine.

Neuroleptic activity was also demonstrated in the test involving inhibition of stereotypy induced by apomorphine in rats. The animals were given the test product by the intraperitoneal route, followed 30 minutes later by 2.5 mg/kg apomorphine by the subcutaneous route. Their behavior was noted for the following 30 minutes. Under these conditions, COR 2865 administered in a dose of 100 mg/kg inhibited 67% of the apomorphine-induced stereotypy.

Hypolipidemic Activity: In mice with hypercholesterolemia produced by a diet high in cholesterol and cholic acid fed for seven days, administration of an oral dose of 100 mg/kg COR 2865 on the sixth and seventh day brought about a reduction in serum cholesterol of 31% and a reduction of HP-betalipoproteins of 38% as well as a decrease in the VLDL+LDL/cholesterol ratio.

Platelet Anti-Aggregation Activity: The products according to the present invention inhibited the platelet aggregation induced by 50 mcg/ml sodium arachidonate with or without 1 mcg/ml aspirin in rabbit plasma with a high platelet content. In the presence of aspirin, this inhibition was 100% in a concentration of 2.5 mcg/ml COR 2860 and a concentration of 5 mcg/ml COR 2864. In the absence of aspirin, the inhibition was 100% with a concentration of 5 mcg/ml COR 2860 and 10 mcg/ml COR 2864.

In view of their low toxicity and their pharmacological properties, especially their alpha-1 blocking and antihypertensive properties, the products according to the present invention can, e.g., be used in the treatment of arterial hypertension, either alone or in combination with a diuretic or other antihypertensive drugs, in the treatment of peripheral vascular disturbances such as acrocyanosis and Raynaud's syndrome and in the treatment of glaucoma.

In view of their platelet anti-aggregation activity, the products according to the present invention are useful in long-term therapy following myocardial infarction.

In view of their hypolipidemic activity, the products according to the present invention are useful in the treatment of hyperlipemia.

In view of their neuroleptic activity, the products according to the present invention are useful in the treatment of psychosis, anxiety states and states of aggressiveness.

In view of their anticalcium properties, the products according to the present invention can be used, e.g., in the treatment of angina and cardiac rhythm disturbances.

In view of their antiallergy and antihistamine properties, the products according to the present invention can be used in the treatment of allergic conditions.

The dosage and therapeutic schedule will be a function of the subject and condition to be treated. It will be possible to administer the products orally (e.g., in the form of gelatin-coated capsules, tablets, ingestable drops), by the parenteral route (solution for intramuscular or intravenous injection; solution for intravenous perfusion), by the rectal route (suppositories), and locally (collyria for glaucoma therapy, creams, ointments, gels). Depending on the indications, the daily dose will range from 1–100 mg in one to three administrations for the oral route, from 1–100 mg for one or two administrations by the rectal route and 0.1–10 mg for intravenous administration. The collyria will contain 0.05–0.5% of the active principle and the ointments, creams and gels will contain 0.5–5% of the active principle.

Many modifications and variations of the present invention are possible in light of the above teachings. Therefore, it is to be understood that within the scope of the appended claims, the invention may be practiced otherwise than as specifically described.

What is claimed as new and desired to be secured by letters patent of the United States is:

1. Compounds of the formula (I):

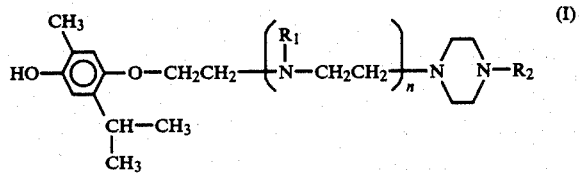

wherein n is 0 or 1, $R_1$ is H or a lower alkyl of 1 to 6 carbon atoms, $R_2$ is an unsubstituted phenyl group or a phenyl group substituted by one or two of the same or different substituents selected from the group consisting of hydroxy, lower alkyl of 1 to 6 carbon atoms, lower alkoxy of 1 to 6 carbon atoms, chloro, fluoro, trifluoromethyl or a 2-, 3- or 4- pyridyl ring, in the form of a free base or a pharmaceutically acceptable acid addition salt thereof.

2. The compounds of claim 1, wherein n is 0.

3. The compounds of claim 2, wherein $R_2$ is selected from the group consisting of 2-methoxyphenyl, phenyl, 3-trifluoromethyl phenyl, 4-fluorophenyl, 3-chlorophenyl, 2-methylphenyl, 2,3-dimethylphenyl, 2-chlorophenyl, 3-ethoxyphenyl, 2-pyridyl, 2-propoxyphenyl and 2-hydroxyphenyl.

4. The compounds of claim 1, wherein n is 1.

5. The compounds of claim 4, wherein $R_1$ is methyl and $R_2$ is phenyl and 2-methoxyphenyl.

6. A pharmaceutical composition for effecting hypolipidemic therapy or cardiovascular therapy, comprising an effective amount of one or more of the compounds of claim 1 and a pharmaceutical excipient or diluent.

7. A method of effecting cardiovascular therapy which comprises administering an effective amount of at least one compound of claim 1.

8. A method of effecting hypolipidemic therapy which comprises administering an effective amount of at least one compound of claim 1.

* * * * *